United States Patent [19]
Bartley

[11] Patent Number: 5,342,987
[45] Date of Patent: Aug. 30, 1994

[54] ALKENYL ALKANOATE PRODUCTION

[75] Inventor: William J. Bartley, Charleston, W. Va.

[73] Assignee: Union Carbide Chemicals & Plastics Technology Corporation, Danbury, Conn.

[21] Appl. No.: 952,280

[22] Filed: Sep. 28, 1992

Related U.S. Application Data

[60] Division of Ser. No. 793,129, Nov. 18, 1991, Pat. No. 5,179,057, which is a continuation-in-part of Ser. No. 696,215, May 6, 1991, Pat. No. 5,185,308.

[51] Int. Cl.$^5$ .............................................. C07C 67/05
[52] U.S. Cl. .......................................................... 560/245
[58] Field of Search ............................................ 560/245

[56] References Cited

U.S. PATENT DOCUMENTS

| | | | |
|---|---|---|---|
| 3,743,607 | 7/1973 | Sennewald et al. | 252/430 |
| 3,822,308 | 7/1974 | Kronig et al. | 260/497 |
| 4,048,096 | 9/1977 | Bissot | 252/430 |
| 4,087,622 | 5/1978 | Nakamura et al. | 560/245 |

FOREIGN PATENT DOCUMENTS

| | | |
|---|---|---|
| 0747415 | 11/1966 | Canada . |
| 1215210 | 12/1970 | United Kingdom . |
| 1511869 | 5/1978 | United Kingdom . |

OTHER PUBLICATIONS

Journal of Catalysis, vol. 17, pp. 366-374, 1970 (Nakamura et al.).
Chemical Abstracts vol. 115(14):136969y (1991).
Chemical Abstracts vol. 70(9):37210q (1969).
Chemical Abstracts vol. 75(14):89050k (1971).

*Primary Examiner*—Michael L. Shippen
*Attorney, Agent, or Firm*—E. C. Trautlein

[57] ABSTRACT

This invention provides a process for producing improved catalysts for the production of alkenyl alkanoates by the reaction of an alkene, an alkanoic acid and an oxygen-containing gas. The catalysts contain palladium, gold and a potassium promoter and are characterized by a reduced sodium content which results in increased catalyst activity. The reduced sodium content is obtained by washing the catalyst, at a particular intermediate point in its production, with a cation exchange solution.

1 Claim, 4 Drawing Sheets

ALKENYL ALKANOATE PRODUCTION

This application is a division of U.S. patent application No. 07/793,129 filed Nov. 18, 1991 (now U.S. Pat. No. 5,179,057) which was a continuation in part of U.S. patent application Ser. No. 696,215; filed May 6, 1991 (now U.S. Pat. No. 5,185,308).

FIELD OF THE INVENTION

This invention relates to a process for producing catalysts for the production of alkenyl alkanoates from alkenes, alkanoic acids and an oxygen-containing gas, to the catalysts so produced (hereinafter referred to as "alkenyl alkanoate catalysts") and to a process for producing alkenyl alkanoates using such catalysts.

DESCRIPTION OF THE RELATED ART

Processes for producing alkenyl alkanoate catalysts are known. By way of illustration, British Patent 1,215,210 (National Distillers) discloses a process for the production of olefinically unsaturated carboxylic esters (e.g., vinyl acetate) comprising reacting an olefinically unsaturated compound, a carboxylic acid and oxygen in the presence of a catalyst containing palladium metal and platinum metal and activated with at least one alkali metal or alkaline earth metal hydroxide or organic acid salt or inorganic acid salt.

The alkenyl alkanoate catalysts of National Distillers are produced by: (1) dissolving salts of the metals in conventional solvents, (2) spraying the solutions on an inert carrier or soaking the inert carrier in the solutions, (3) removing the solvent, (4) converting the salts so deposited on the carrier to the free metals by (a): thermal decomposition, (b) by reduction with hydrogen or (c) by reduction in suspension using aqueous alkaline formaldehyde, aqueous hydrazine or aqueous or alcoholic sodium borohydride, (5) washing the catalyst with water to remove chlorides (see the National Distillers Examples) and (6) activating the catalyst. In the National Distillers catalyst preparation procedure, there is no precipitation of the metal salts on the carrier prior to their conversion to the free metals.

The National Distillers' alkenyl alkanoate catalysts are activated with a minor amount of at least one alkali metal or alkaline earth metal hydroxide or organic acid salt or inorganic acid salt. The alkali metal or alkaline earth metal salts of weak acids, both organic and inorganic acids are stated to be especially useful as activators. Sodium, lithium, potassium, rubidium and cesium salts and mixtures thereof are stated to be most effective as activator and the use of sodium and potassium salts, e.g., sodium and potassium acetates is especially preferred. The salts may have such anions as citrate, acetate, borate, phosphate, tartrate, benzoate or aluminate. National Distillers discloses that alkali metal and alkaline earth metal hydroxides are also effective activators and that the use of halide anions should preferably be avoided, since the presence of halides is stated to deleteriously affect the synthesis reaction.

In both of the National Distillers' Examples the salts were reduced with hydrogen and washed with water to remove chlorides. Then the catalysts were treated with aqueous solutions containing both sodium acetate and potassium acetate and dried in a rotary evaporator and then under vacuum. Based on the amount of sodium acetate used, the resulting catalysts contained about 0.23 weight percent sodium. The most active catalyst of the National Distillers' Examples (i.e., the catalyst of Example 2H) is disclosed as having an activity of 8.3 grams of vinyl acetate per gram of palladium per hour (equivalent to about 165 grams of vinyl acetate per liter of catalyst per hour, assuming a catalyst density of one gram per milliliter).

As another illustration, Journal of Catalysis, volume 17, pages 366 to 374, 1970 (Nakamura et al.) discloses vinyl acetate catalysts produced by impregnating a carrier (calcined alumina) with an aqueous solution of palladium chloride, evaporating to dryness, reducing with an alkaline hydrazine hydrate solution, washing with distilled water to remove chloride ions, impregnating with a metal salt solution (e.g., a potassium or sodium acetate solution) and drying. Nakamura et al. reports that impregnating with potassium acetate results in a catalyst activity of 25 grams of vinyl acetate per hour per liter of catalyst while impregnating with sodium acetate results in a catalyst activity of 19 grams of vinyl acetate per hour per liter of catalyst.

As a further illustration, U.S. Pat. No. 3,743,607 (Sennewald et al.) discloses a process for making vinyl acetate from ethylene, acetic acid, and molecular oxygen or air in the gas phase. A mixture of these reactants is passed in contact with a supported catalyst containing metallic palladium, an alkali metal formate or acetate, and metallic gold.

The vinyl acetate catalysts of Sennewald et al. are produced by impregnating a catalyst carrier with an aqueous solution of a palladium salt and a gold salt and the resulting mixture is evaporated to dryness. The mass so obtained is introduced into an aqueous solution containing an appropriate reducing agent (e.g., hydrazine) that is capable of reducing both the palladium and gold salts to the metallic state. In the Sennewald et al. catalyst preparation procedure, there is no precipitation of the salts on the carrier prior to the reduction. Once the reduction is complete, the catalyst mass is removed from the liquid by filtration and washed with water. When the reduction is achieved by means of a reducing agent free of alkali (e.g., hydrazine), the catalyst is conveniently impregnated with an about 10% solution of sodium acetate. The formates or acetates Of lithium or potassium can also be used. The catalyst is then dried and is ready for use. Sennewald et al. discloses that, in the absence of such treatment, despite the gold it contains, the catalyst is found to have a substantially lower activity (e.g. of only 15 grams vinyl acetate per liter of catalyst per hour) instead of the activity of 50 to 120 grams vinyl acetate per liter of catalyst per hour disclosed in Sennewald et al. for the Sennewald et al. catalysts. Catalysts which have been reduced by means of a composition comprising sodium formate and formic acid are disclosed to be active, even if no sodium acetate has been added thereto.

Sennewald et al. states that it has unexpectedly been found that the vinyl acetate space/time yields and, more particularly, the lifetime of the supported catalyst until regeneration thereof, can be substantially increased when the catalyst is impregnated with a solution prepared from a mixture of various acetates of sodium, potassium, rhodium or cesium instead of impregnation with a solution of a single alkali metal acetate.

The highest activity reported in the Sennewald et al. Examples is in Example 11 where a catalyst was impregnated with sodium and potassium acetate as described Example 9 of Sennewald et al. To effect the impregnation the catalyst was introduced into a solution of the acetates, the supernatant solution was decanted and the catalyst was dried. The catalyst so obtained in Example 11 of Sennewald et al. is reported to contain about 0.8% sodium and to have an activity of 146 grams of vinyl acetate per liter of catalyst per hour. The other Sennewald et al. Examples (including Examples 4, 5 and 12(e) where the catalysts were apparently substantially free of sodium) reported even lower catalyst activities than Example 11. The catalysts of Sennewald et al. Examples 4 and 9 were reported to have the same palladium and gold contents and approximately the same activities. The catalyst of Example 4 is reported to contain 2.5% potassium (as potassium acetate) while the catalyst of Example 9 is reported to contain about 1.8% sodium (as sodium acetate).

U.S. Pat. No. 3,822,308 (Kronig et al.) discloses that particularly active supported catalysts containing palladium and gold for the production of vinyl esters from ethylene, lower carboxylic acids with 2 to 4 carbon atoms and oxygen in the gas phase at elevated temperature and at normal or elevated pressure are obtained by the following process. The catalyst support is treated, simultaneously or successively, with or without intermediate drying, with a solution ("Solution A") containing dissolved salts of palladium and gold and, optionally, salts of other metals, and another solution ("Solution B") containing compounds (hereinafter referred to as "precipitating agents") which are able to react on the catalyst support with the noble metal salts of the Solution A to form water-insoluble noble metal compounds which are practically free from halogen, sulphur and nitrogen. Solutions A and B (separately or in combination) are used to impregnate the catalyst support in quantities which correspond to from 10 to 110% of the absorptive capacity of the catalyst support for these solutions. The catalyst support impregnated with Solutions A and B is subjected to a time/temperature treatment such that at least 95% of the impregnated palladium and at least 95% of the impregnated gold are transformed into water-insoluble noble metal compounds. The water-insoluble noble metal compounds are largely transformed by treatment with reducing agents into the noble metals and the water-soluble compounds which are contained in the catalyst are removed by washing, before or after the reduction.

In a preferred embodiment of the Kronig et al. process, alkali metal carboxylates (especially alkali metal acetates) are applied on the catalyst before or after the treatment with reducing agents in such quantities that the catalyst, after being dried, contains from 1 to 30% by weight of alkali metal carboxylate. Examples of the alkali metal carboxylates disclosed in Kronig et al. include sodium formate, potassium acetate, sodium acetate, lithium acetate, potassium propionate and potassium butyrate.

The Kronig et al. Examples employing precipitating agents report catalyst activities markedly higher than the activities reported by National Distillers and Sennewald et al. where no precipitating agents are used. Thus, Kronig et al. Example 1 employs sodium hydroxide as a precipitating agent and potassium acetate as a promoter and reports a activity of 452 grams of vinyl acetate per hour per liter of catalyst. Kronig et al. Example 3 employs potassium carbonate as a precipitating agent and an "alkali metal acetate" as a promoter and reports that the results obtained with the catalyst were comparable to those of Kronig et al. Example 1.

U.S. Pat. No. 4,048,096 (Bissot) discloses a catalyst having a specific activity of at least about 83 grams of vinyl acetate per gram of precious metal per hour measured at 150° C. The Bissot vinyl acetate catalyst consists essentially of: (1) a catalyst support having a particle diameter of from about 3 to about 7 mm and a pore volume of from about 0.2 to about 1.5 ml./g., a 10% by weight water suspension of the catalyst support having a pH of from about 3.0 to about 9.0; (2) a palladium-gold alloy distributed in a surface layer of the catalyst support, the surface layer extending less than about 0.5 mm from the surface of the support, the palladium in the alloy being present in an amount of from about 1.5 to about 5.0 grams per liter of catalyst, and the gold being present in an amount of from about 0.5 to about 2.25 grams per liter of catalyst, and (3) from about 5 to about 60 grams per liter of catalyst of alkali metal acetate. Bissot discloses that the palladium is the active catalyst metal and the gold is a catalyst promoter.

Bissot also discloses a process for preparing the Bissot catalyst. Like Kronig et al., the Bissot process involves precipitation of the metal salts on the catalyst support. The Bissot process comprises: (1) impregnating the catalyst support with aqueous solution of water-soluble palladium and gold compounds, (2) precipitating water-insoluble palladium and gold compounds on the catalyst support by contacting the impregnated catalyst support with a solution of compounds (preferably sodium metasilicate) capable of reacting with the water-soluble palladium and gold compounds to form water-insoluble palladium and gold compounds, (3) converting the water-insoluble palladium and gold compounds into palladium and gold metal on the support by treatment with a reducing agent, (4) washing the catalyst with water, (5) drying the catalyst (see Example 1 of Bissot), (6) impregnating the catalyst with an alkali metal acetate promoter (e.g., a potassium promoter), and (7) drying the catalyst.

The improvement disclosed in Bissot involves distributing the palladium and gold as an alloy in a surface layer of the catalyst support, the surface layer extending less than about 0.5 millimeter from the surface of the support. The impregnating step is carried out with an aqueous solution of palladium and gold compounds and the total volume of the solution is from about 95 to about 100% of the absorptive capacity of the catalyst support. The precipitating step in Bissot is carried out by soaking the wet catalyst support with a solution of an alkali metal silicate, the amount of alkali silicate being such that, after the alkali metal silicate solution has been in contact with the catalyst support for about 12 to 24 hours, the pH of said solution is from about 6.5 to about 9.5.

Bissot does not report the sodium content of the catalysts of the Bissot Examples. Bissot Example 1 reports that the catalyst of that Example had an activity of 560 grams of vinyl acetate per liter of catalyst per hour. In Example XXVII below, two catalysts produced following the disclosure of Example 1 of Bissot were found to have sodium contents of 0.32 and 0.38 weight percent and activities of 551 grams and 535 of vinyl acetate per liter of catalyst per hour.

Despite the foregoing prior art processes, it is desirable to further improve the activity of alkenyl alkanoate catalysts.

SUMMARY OF THE INVENTION

This invention is based, in part, on the discovery that the activity of alkenyl alkanoate catalysts is increased if the sodium content thereof is decreased by washing the catalysts, at a particular intermediate point in their production, with a cation exchange solution.

More specifically, this invention provides a process for producing a catalyst that is useful in catalyzing the reaction of an alkene, an alkanoic acid and an oxygen-containing gas to produce an alkenyl alkanoate and that comprises support particles which are capable of exchanging cations and which are impregnated with palladium, gold and potassium acetate, said process comprising the steps of:

(a) impregnating the support particles with aqueous solutions of water-soluble palladium and gold compounds;

(b) precipitating water-insoluble palladium and gold compounds onto the support particles from such solutions using a precipitating agent;

(c) converting the precipitated water-insoluble palladium and gold compounds to palladium and gold on the support particles using a reducing agent so as to produce an impregnated support containing sodium owing to the presence of sodium in one or more of the materials used in steps (a) to (c);

(d) washing the impregnated support particles with a cation exchange solution so that the amount of sodium in the catalyst is reduced and the activity of the catalyst is increased; and (e) drying the washed and impregnated support particles to produce the catalyst.

If it is desired to increase further the activity of the catalyst produced by the process of this invention, the above steps can be followed by the steps of:

(f) impregnating the dried support particles with a potassium promoter; and (g) drying the catalyst (see Run I-2A below and FIG. 1).

However, such further increase in the activity of the catalyst is preferably achieved as described below in connection with the preferred embodiment of this invention which involves the use of particular concentrations and amounts of particular cation exchange solutions (i.e. potassium promoter solutions) for that purpose (see also Examples VII to XII below and FIG. 3).

This invention also provides alkenyl alkanoate catalysts having reduced sodium contents and a process for producing alkenyl alkanoates using such catalysts.

Without wishing to be bound by any particular theory, it is believed that sodium impurities in alkenyl alkanoate catalysts reduce the activity of the catalysts and that the cations in the cation exchange solutions used in step (d) of the process of the present invention displace sodium (and perhaps other ion-exchangeable impurities) from the supports so that the impurities can be washed from the supports in step (d). As a result of the reduction in sodium content, the activity of the catalysts is increased.

DESCRIPTION OF THE PREFERRED EMBODIMENTS

PROCESS FOR PRODUCING CATALYSTS

The cation exchanged solutions employed in the process of this invention for producing alkenyl alkanoate catalysts are solutions which contain a cation that exchanges with sodium on the support and which does not impair, and preferably promotes, the activity of the catalyst. Suitable cation exchange solutions include, but are not limited to, solutions of potassium promoters. Preferred cation exchange solutions are aqueous solutions containing from 0.01 to 20 weight percent of a compound containing a suitable cation. Such compounds include, but are not limited to, potassium acetate, lithium acetate, potassium nitrate, potassium carbonate, ammonium carbonate, ammonium acetate, and magnesium acetate. More preferred are solutions containing from 0.1 to 10 weight percent (and most preferred from 0.5 to 7 weight percent) of the compound containing a suitable cation.

In order to economize on the amount of the compound containing the cation in the cation exchange solutions used in the process of this invention for producing alkenyl alkanoate catalysts, the washing with the cation exchange solution can be preceded by one or more washes with water to remove impurities that are not strongly associated with the support (e.g., chlorides and unbound sodium).

The optimum concentration of the ion exchange solution used in the process of this invention for producing alkenyl alkanoate catalysts will depend on factors such as the sodium content in the catalyst, the volume of wash solution employed, the total washing time, etc. and is best determined by experimentation. Concentrations of the compound containing a suitable cation of about 10% or higher are less preferred because they are wasteful of the compounds and sometimes give catalysts having lower activities.

The potassium promoters used in step (d) or in step (f) of the process of this invention for producing alkenyl alkanoate catalysts include potassium alkanoates and any potassium compound that is converted to a potassium alkanoate during the alkenyl alkanoate-forming reaction (i.e., the reaction of an alkene, an alkanoic acid and an oxygen-containing gas in the presence of the catalyst to produce an alkenyl alkanoate). Suitable potassium compounds include potassium acetate, bicarbonate, nitrate and (when a stable support is used) hydroxide. The promoters are preferably used in the form of aqueous solutions.

When the cation in the cation exchange solution used in step (d) in the process of the present invention for producing alkenyl alkanoate catalysts is potassium, potassium is thereby introduced into the catalyst. In such cases, the catalyst should be dried and analyzed for potassium to determine how much more potassium should be added in step (f). This procedure is necessary to avoid producing a catalyst having an excess or a deficiency of potassium, either of which can cause a decrease in catalyst activity.

The preferred embodiment of the process of the present invention for producing alkenyl alkanoate catalysts involves using a solution of the potassium promoter as the cation exchange solution in step (d) and employing a sufficient concentration and amount of the potassium promoter solution in that step so that the potassium acetate impregnation step [step (f)] and the second drying step [step (g)] are not required. This embodiment is illustrated in FIG. 3.

More specifically, the preferred embodiment of the process of the present invention for producing alkenyl alkanoate catalysts comprises the steps of:

(a) impregnating the support particles with aqueous solutions of water-soluble palladium and gold compounds;

(b) precipitating water-insoluble palladium and gold compounds onto the support particles from such solutions using a precipitating agent;

(c) converting the precipitated water-insoluble palladium and gold compounds to palladium and gold on the support particles using a reducing agent, said impregnated support containing sodium owing to the presence of sodium in one or more of the materials used in steps (a) to (c);

(d) washing the support particles with a potassium promoter solution in a concentration and in an amount sufficient both: (I) to reduce the amount of sodium in the catalyst so as to increase the activity of the catalyst and (II) to further impregnate the catalyst with the amount of potassium necessary to further promote the activity of the catalyst; and (e) drying the washed and further impregnated support particles to produce the catalyst.

The appropriate potassium promoter concentration in the cation exchange solution used in the washing step (d) of the preferred embodiment of this invention will depend upon such factors as the ion exchange properties of the support material and its pore volume and the desired activity of the catalyst. For this reason, the optimum concentration is best determined by routine experimentation. A five percent aqueous potassium acetate solution has been found to give good results.

When using the catalyst preparation process described in U.S. Pat. No. 4,048,096 (Bissot), some colloidal palladium and gold are washed from the catalyst support during the washing step. Another benefit of the practice of the present invention is a more efficient utilization of metals during catalyst preparation when a potassium acetate solution is used as the cation exchange solution. Surprisingly, no detectable amount of palladium or gold is removed from the catalyst support when the potassium acetate solution is employed as the cation exchange solution in the practice of the present invention. Examples I-1A and I-2A below show that one weight percent of the palladium and gold were washed from the catalyst using the Bissot process but no detectable amounts of these metals were washed out in the process of this invention. This benefit not only results in improved efficiency of metal deposition but also serves to reduce the cost of recovery of the precious metals from the washings.

The support particles used in the process of this invention for producing alkenyl alkanoate catalysts are solid particulate materials that are capable of exchanging cations, that are capable of being impregnated with palladium, gold and a potassium promoter and that are inert under the conditions used to produce alkenyl alkanoates. Illustrative of such support particles are particulate silica, alumina, and silica-aluminas. Silica is the preferred support. The support preferably has a surface area from 100 to 800 square meters per gram.

The aqueous solutions of water-soluble palladium and gold compounds used in the process of this invention for making alkenyl alkanoate catalysts include aqueous solutions of any suitable palladium or gold compound such as palladium (II) chloride, sodium tetrachloropalladium (II) ($Na_2PdCl_4$), palladium (II) nitrate, palladium (II) sulfate, gold (III) chloride or auric (III) acid ($HAuCl_4$). The volume of the solution preferably corresponds to from 95 to 100% (more preferably from 98 to 99%) of the pore volume of the support.

The precipitating agents used in the process of the present invention for producing alkenyl alkanoate catalysts include sodium, lithium and potassium silicates and hydroxides. The precipitating agents are preferably employed in the form of an aqueous solutions containing a 1.6 to 1.8 molar excess of the precipitating agents. The volume of such solutions used is preferably just sufficient to cover the support particles.

The reducing agents used in the process of this invention for producing alkenyl alkanoate catalysts include hydrazine, ethylene, formaldehyde, hydrogen and sodium borohydride. The reducing agents are preferably employed in the form of an aqueous solutions containing a 50:1 (or more preferably a 10:1) molar excess of the reducing agents. If hydrogen is used, it is usually necessary to heat the catalyst to 100° to 300° C. to complete the reduction.

The washing step [step (d)] used in the process of this invention for producing alkenyl alkanoate catalysts can be conducted batchwise or continuously. Continuous washing is more efficient but may not be most suitable for large scale (e.g., plant scale) catalyst production. In continuous washing, the cation exchange solution is slowly and continuously passed through the catalyst over a period of time (e.g. for from 8 to 24 hours). In batch washing, the catalyst is contacted with the cation exchange solution, the mixture is allowed to stand (e.g., for from 0.5 to 2.0 hours) and the solution and catalyst are separated. In batch washing, several such washes (e.g., from 2 to 10, or preferably from 4 to 6 washes) are often required to reduce the sodium content of the catalyst to the desired level. Temperatures from 20° C. to 80° and ratios of cation exchange solution to catalyst of from 2:1 to 100:1 can be used in either batch or continuous washing.

The washing of the catalyst with a cation exchange solution in accordance with step (d) of the process of this invention for producing alkenyl alkanoate catalysts is distinct from the potassium promoter impregnation steps of prior art processes for producing alkenyl alkanoate catalysts. Such prior art impregnation steps are conducted by the incipient wetness technique or the decantation technique. In the incipient wetness technique [see the Example 5 of British Patent 1,215,210 (National Distillers)], the catalyst is contacted with the minimum amount of aqueous potassium promoter solution required to fill the pores of the support and to impregnate the catalyst with the desired amount of potassium promoter. Then the water is evaporated. No sodium can be removed from the catalyst by that technique. In the decantation technique, the (preferably dry) catalyst is immersed in a larger volume of the aqueous potassium promoter solution than is used in the incipient wetness technique. After the pores are filled with the solution, the excess solution is decanted and the catalyst is dried. Only one immersion and decantation operation is conducted and the contact time is relatively short. Hence, only a minimal amount of sodium can be removed from the catalyst by the decantation technique. Example 9 of U.S. Pat. No. 3,743,607 (Sennewald et al.) illustrates the decantation technique using a moist catalyst.

The drying of the catalyst in accordance with step (e) of the process of this invention for producing alkenyl alkanoate catalysts can be conducted in any convenient manner. By way of illustration, drying can be conducted at 40° C. to 120° C. in a forced air oven for 15 to 30 hours. Other processes for producing alkenyl alkanoate catalysts having reduced sodium content (and so increased catalyst activity) are described and claimed in U.S. patent application Ser. No. 973,127; filed Nov. 18, 1991 (now U.S. Pat. No. 5,189,004) and in U.S. patent application Ser. No. 793,131; filed Nov. 12, 1991 (now U.S. Pat. No. 5,179,056).

CATALYST COMPOSITIONS

The catalyst of this invention are useful in catalyzing the reaction of an alkene, an alkanoic acid and an oxygen-containing gas to produce an alkenyl alkanoate and comprise support particles which are capable of exchanging cations and which are impregnated with precipitated and reduced palladium and gold and a potassium promoter, any sodium in the catalyst being present in an amount desirably no more than 0.3 weight percent based on the total weight of the catalyst.

The catalysts of this invention preferably have a palladium content of greater than 0.25 weight percent based on the total weight of the catalyst, more preferably greater than 0.5 weight percent based on the total weight of the catalyst and most preferably from 0.5 to 1.7 weight percent based on the total weight of the catalyst. It is preferred that the gold to palladium weight ratio of the catalyst is from 0.2 to 1.5 and, most preferably, from 0.4 to 1.2.

It is preferred that the catalysts of this invention are shell-impregnated catalysts wherein a catalyst support has a particle diameter from about 3 to about 7 millimeters and a pore volume of 0.2 to 1.5 milliliters per gram. The palladium and gold are preferably distributed in the outermost 1.0 millimeter thick layer of the catalyst support particles. The catalysts preferably contain from about 1.4 to about 3.8 weight percent (more preferably from 2 to 3.6 weight percent) of potassium derived from the potassium promoter.

The catalysts of this invention have reduced sodium contents. Preferably, the catalysts contain no more than 0.3 weight percent sodium based on the weight of the catalyst. More preferably, the catalysts contain no more than 0.2 weight percent sodium and, most preferably, the catalysts contain no more than about 0.1 weight percent sodium based on the weight of the catalyst. The amount of sodium in the catalysts of this invention will depend upon such factors as the starting materials used, the number of washes, the total wash time, the volume of washing solutions and the concentration of the cation in the cation exchange solution.

The catalysts of this invention can be produced by the above-described process of this invention and by the processes described in the U.S. Pat. No. 5,189,004 and U.S. Pat. No. 5,179,056.

PROCESS FOR PRODUCING ALKENYL ALKANOATES

The process of the present invention for producing alkenyl alkanoates comprises reacting an alkenyl, an alkanoic acid, and an oxygen-containing gas in the presence of a catalytic amount of catalyst of this invention as described above. The process is preferably conducted at a temperature from 100° C. to 250° C. (and most preferably at a temperature from 140° C. to 200° C.) and at a pressure from 15 psi to 300 psi (most preferably at a pressure from 90 pounds per square inch to 150 pounds per square inch.) The process is preferably conducted continuously in the vapor phase.

The process of this invention for producing alkenyl alkanoates is characterized by the greater activity of the catalyst. Typically the activity of the catalysts is 5% to 25% greater (in terms of quantity of alkenyl alkanoate produced per unit of catalyst per unit time) as compared to otherwise identical catalysts containing from over 0.3 to about 1.0 weight percent sodium. Although catalyst selectivity (i.e., the tendency to produce alkenyl alkanoates rather than by-products such as carbon dioxide) declines somewhat with decreasing sodium content, that disadvantage is more than offset by increased catalyst activity, particularly in the range of sodium contents found in commercial alkenyl alkanoate catalysts (e.g., up to about 1.0 weight percent sodium).

Preferred alkanoic acid starting materials used in the process of this invention for producing alkenyl alkanoates contain from two to four carbon atoms (e.g., acetic, propionic and butyric acid). Preferred alkene starting materials contain from two to four carbon atoms (e.g. ethylene, propylene and n-butene). Preferred products of the process are vinyl acetate, vinyl propionate, vinyl butyrate, and allyl acetate.

One aspect of the process of this invention for producing alkenyl alkanoates involves the use of the models shown in Table G below to predict the oxygen conversion to vinyl acetate, the activity of the catalyst, the selectivity of the catalyst to vinyl acetate, the production of ethyl acetate by-product and/or the production of heavy by-products.

The alkenyl alkanoates produced by the process of this invention are known compounds having known utilities (e.g., vinyl acetate is useful in producing polyvinyl acetate).

EXAMPLES

In the following Examples, the following abbreviations are used:

| Abbreviation | Meaning |
| --- | --- |
| Support I | Silica beads having an average diameter of 5 to 6 millimeters and containing about 0.1 weight percent sodium. The beads have a surface area from 150 to 200 square meters per gram and a pore volume from 0.6 to 0.7 milliliters per gram. Support I contains SiOH groups that are capable of exchanging cations. Support I is sold by Sud Chemie AG as "KA-160" |
| Catalyst I | A catalyst illustrating the prior art prepared in accordance with Catalyst Preparation Procedure described below using sodium metasilicate as the precipitating agent and the Column Washing Procedure. |

| | -continued |
|---|---|
| Catalyst II | A larger scale (20 liter) pilot plant preparation of Catalyst I using sodium hydroxide as the precipitating agent and the Batch Washing Procedure described below. |
| STY* | Space Time Yield (a measure of catalyst activity) expressed as grams of vinyl acetate per liter of catalyst per hour. |
| % Selectivity* | Selectivity was calculated as follows: Selectivity = 100 × (moles vinyl acetate)/(moles vinyl acetate + ½ × moles $CO_2$) |

*All the values for activites and selectivities reported in the Examples appearing below are based on the activities and selectivities measured twenty-six hours after full oxygen feed was reached in the Catalyst Test Method described below.

| | |
|---|---|
| AA Analysis | Atomic Adsorption Spectroscopy |
| ICP | Inductively Coupled Plasma Optical Emission Spectrometry |
| g VA/l cat/hr | grams of vinyl acetate produced per liter of catalyst per hour |
| VA | vinyl acetate |
| EtOAc | ethyl acetate |
| KOAc | potassium acetate |
| NaOAc | sodium acetate |
| % | percent by weight |
| g | grams |
| ml | milliliter |
| mm | millimeter |
| hrs | hours |
| min | minute |

In the following Examples, the following procedures were used:

Catalyst Preparation Procedure

A. Support I (15 g) was added to a solution of $Na_2PdCl_4$ (35.86% Pd, 0.258 g) and $HAuCl_4$ (48.95% Au, 0.094 g) dissolved in 9.0 ml of deionized water. The mixture so formed was gently agitated until all of the moisture was absorbed into the support and then was allowed to stand in a sealed flask for about one hour at room temperature so as to impregnate the support with the palladium and gold salts. The damp catalyst was covered with a solution of either sodium hydroxide (0.236 g in 28 ml water) or sodium metasilicate, $Na_2SiO_3$, (0.837 g in 28 ml water) as a precipitating agent. After mixing for a few seconds, the mixture was allowed to stand covered and undisturbed for 23 hours at room temperature to deposit water-insoluble palladium and gold compounds on the support. The palladium and gold were then reduced by the addition of 1.0 g of 85% hydrazine hydrate to the above mixture. The mixture was agitated for a few seconds and allowed to stand covered and undisturbed at room temperature for another 23 hours. The supernatant liquid was decanted from the catalyst and the catalyst was rinsed four times with water to remove the small amount of metal sludge present. The catalyst was washed thoroughly by either the Column Washing Procedure or the Batch Washing Procedure described below. The catalyst was dried on a stainless steel screen at 60° C. in a forced air oven for 20 to 24 hours. In practice the preferred embodiment of this invention, the Catalyst Preparation Procedure was complete at this point.

B. In the practice of other embodiments of this invention and in the practice of the prior art procedures and comparative Examples described below, the Catalyst Preparation Procedure also involved the following additional steps: The catalyst was analyzed for potassium using AA Analysis. Then the catalyst was impregnated with the desired amount of potassium acetate in water using the impregnation technique described above for the palladium and gold salts. The impregnated catalyst was then dried at 60° C. for 20 to 24 hours.

C. The palladium, gold, sodium, and potassium contents in the finished catalysts were determined by ICP analyses. In most cases, sodium and potassium were also determined by AA Analyses for greater accuracy.

D. Unless otherwise noted, the foregoing procedure was used to prepare all the catalysts referred to in the following Examples. When different quantities of support were used, the quantities of the other starting materials used were varied correspondingly.

E. All the catalysts produced as described in the Examples appearing below were shell impregnated (i.e., substantially all of the palladium and gold was present in a shell within 0.5 mm of the surface of the beads of Support I).

Catalyst Washing Procedures

A. Column Washing Procedure

Catalysts were washed in a 1.24 inch o.d. × 24 inches glass chromatography column fitted with a Teflon® stopcock. Typically 15 g of catalyst was added to the column which was then filled with wash liquid. The stopcock was adjusted to allow the liquid to flow from the column such that about one liter passed through the catalyst at room temperature over a period of about 24 hours. After this period, the excess liquid was drained from the column and the catalyst removed and dried as described above in the Catalyst Preparation Procedure.

B. Batch Washing Procedure

Catalysts were washed in the same column apparatus described above for the Column Washing Procedure. In this variation, the column was filled with just enough wash liquid to cover the catalyst and was then allowed to stand at room temperature for a specified period. The stopcock was opened and the liquid drained. The catalyst was again covered with wash liquid and allowed to stand as before. Washing was continued in this manner for a total of five washes. The total elapsed time was typically 8 hours. After washing, the excess liquid was drained and the catalyst removed and dried as in the Catalyst Preparation Procedure described above.

Catalyst Test Method

The catalyst (2.5 g samples of 5 to 6 mm catalyst spheres) was diluted with 10.5 ml of 0.5 mm glass beads and the mixture was uniformly distributed in both legs of a 316-stainless steel U-tube reactor. The reactor had an outside diameter of ⅜ inch and an overall height of about 6 inches. An ethylene flow of 151 ml/min. was started through the reactor after which the catalyst was heated in an oven maintained at 150° C. while allowing the system to pressurize to 115 psig. After maintaining at these conditions for 1.5 hours, acetic acid vapor was added to the ethylene and the mixture was passed over the catalyst for 45 minutes. Air was added to the feed gas at a slowly increasing rate over a 45-minute period until a total flow of 105 ml./min. was reached. The catalyst was allowed to stabilize for two hours before beginning data collection. The final gas composition was ethylene:acetic acid:oxygen:nitrogen=52.9:10.7:7.7:28.7, the total gas hourly space velocity was about 3800 hr$^{-1}$, and the acetic acid liquid hourly space velocity was about 1 hr$^{-1}$. The product was analyzed by gas chromatography. The run-to-run reproducibility of the microreactors used in these experiments is about ±10 STY units.

EXAMPLE I

Comparative Run I-1A: A 90 g. sample of Support I was impregnated as described in the Catalyst Preparation Procedure using sodium metasilicate as the precipitating agent. After the reduction step, the supernatant liquid was decanted, and the wet beads were divided into three equal portions labeled Samples A, B and C. Samples B and C were retained for later use. Sample A was transferred without drying to the washing apparatus and washed with water using the Column Washing Procedure. The cloudy black washings taken from the column were analyzed by ICP for palladium and gold. The results indicated about 1% of each metal was lost from the catalyst during washing. The catalyst was dried at 60° C. in a forced-air oven for 4.5 hrs. then analyzed for potassium (0.31 wt%). The catalyst (30.4 g) was impregnated with a solution of 1.62 g of potassium acetate in 18.3 ml of water using the procedure described above under Catalyst Preparation Procedure. After drying at 60° C. for 24 hrs. the catalyst was tested for activity. The results are shown in FIG. 1.

Run I-1B: A portion of the catalyst produced from Sample A described in Run I-1A above was rewashed with water using the Column Washing Procedure and dried. Then an amount of potassium acetate was added to increase the potassium acetate content back to its initial level. The results are shown in FIG. 1.

Run I-2A: Sample B of the still-wet catalyst prepared in Run I-1A above, was washed using the Column Washing Procedure as above with the exception that 1% potassium acetate solution (a cation exchange solution) rather than water was used. The washings were colorless and showed no detectable palladium or gold by ICP. The washed catalyst was dried as above and analyzed for potassium (1.41%). The catalyst was impregnated with a solution of 0.608 g of potassium acetate in 17.8 ml of water then dried at 60° C. for 24 hrs. Test results are provided in FIG. 1.

Run I-2B: A portion of the catalyst from Run I-2A above was rewashed with water using the Column Washing Procedure and dried. Then an amount of potassium acetate was added to increase the potassium acetate content back to its initial level. The results are shown in FIG. 1.

Run I-3: Sample C from Run I-1A above was treated identically to Sample B of Run I-2A above, except 1% potassium hydroxide was substituted for the 1% potassium acetate solution in the washing step. After standing for about 12 hours, it was discovered that the silica support had badly degraded and the catalyst had to be discarded. This experiment shows that, under the conditions used, potassium hydroxide is not suitable for use as a cation exchange solution in the present invention when supports sensitive to strong base are used.

Figure 1:
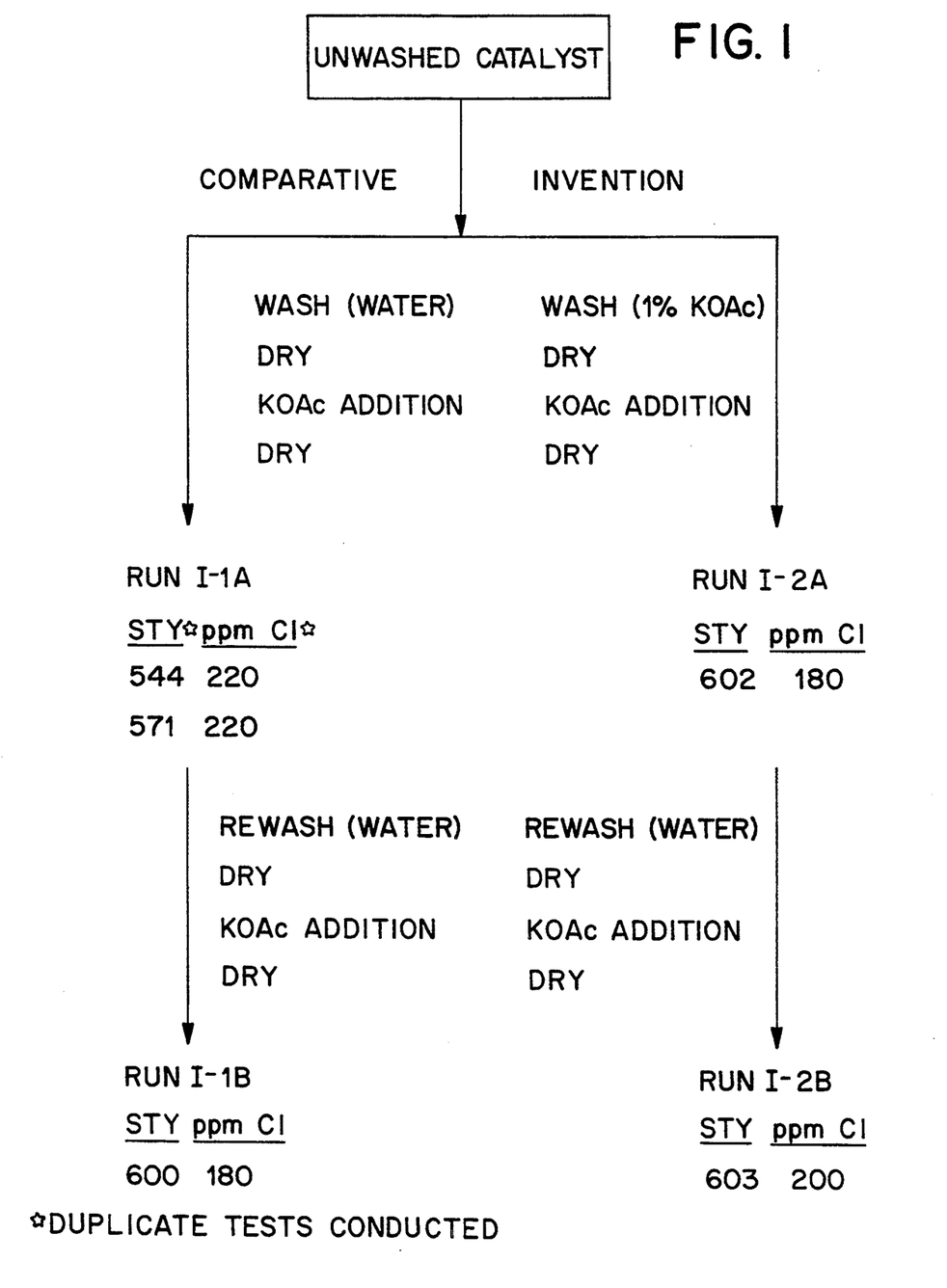
FIG. 1 shows the effect of the washing procedure on catalyst activity in accordance with this invention.

The results in FIG. 1 show that the same activity improvement is obtained by initially using a potassium acetate wash or by using an initial water wash and then rewashing with water after potassium acetate impregnation. These results indicate the presence of a detrimental impurity on the catalyst and support the theory that potassium addition aided in the removal of that impurity.

EXAMPLE II

It was conceivable that chloride was, at least in part, the impurity removed by the experiments described in the above Example I. However, subsequent chloride analyses performed on the catalysts made in Example I (see FIG. 1) indicated only minor differences in chlorine content before and after rewashing. Additional experiments in which varying levels of potassium chloride were added to catalysts also showed a minimal effect on activity (see Table A).

TABLE A

| Effect of Added Chloride | | |
|---|---|---|
| Chloride (ppm) | STY | % Selectivity |
| 0 | 605 | 93.7 |
| 50 | 601 | 93.7 |
| 100 | 598 | 93.5 |

The catalysts used to obtain the results shown in Table A were prepared using the Catalyst Preparation Procedure from the same master batch which had a nominal palladium loading of 0.58%, a Au/Pd ratio of 0.5, a KOAc loading of 5.3%, and an estimated initial chloride content of about 200 ppm. Chloride was added as KCl in the KOAc impregnation solution.

On the basis of the results described above, studies were conducted to determine if other impurities might account for the described effects. Comparison of ICP analytical data from the original catalysts and their rewashed versions revealed significant differences in sodium content but no significant differences in other impurities were observed.

EXAMPLE III

TO test the effect of sodium on catalyst activity, a series of experiments (runs) were conducted where sodium was varied and the potassium level was held constant. In another series of experiments (runs) the sodium to potassium ratio was varied while keeping the total moles of alkali constant. The results of both series of experiments are shown in Table B and the results confirm that increasing levels of sodium do, in fact, result in diminished activity.

In Run 2 of Table B, a rewashed catalyst which was impregnated with a level of sodium similar to that in the original unwashed version (Run 4 of Table B below) showed an appreciably higher activity. This suggests that another detrimental impurity may also be removed by rewashing.

TABLE B

| Effect of Sodium on Catalyst Performance | | | |
|---|---|---|---|
| Run No. | % K | % Na | STY | % Selectivity |
| Constant K content & varied Na content(a) | | | | |
| 1 | 2.24 | 0.117 | 642 | 93.1 |
| 2 | 2.22 | 0.457 | 609 | 93.5 |
| 3 | 2.18 | 0.912 | 540 | 94.1 |
| 4 | 2.31 | 0.453 | 563 | 93.4 |
| Varied Na/K at constant moles alkali(b) | | | | |
| 1 | 2.21 | 0.435 | 616 | 93.6 |
| 2 | 1.77 | 0.705 | 584 | 94.0 |
| 3 | 0.77 | 1.300 | 501 | 94.2 |

(a)Column rewashed Catalyst II was reimpregnated with KOAc and NaOAc solutions.
(b)Prepared by appropriate addition of KOAc and NaOAc to subsamples of a master batch of Catalyst I.

EXAMPLE IV

A series of experiments (Runs IV-1 to IV-4 below) were conducted to further illustrate the effects shown in Example I above. An additional objective was to demonstrate that the benefits of this invention can also be obtained using the Batch Washing Procedure which is more amenable to large-scale catalyst preparation than the Column Washing Procedure which had been used in Example I above.

Comparative Run IV-1: A catalyst was prepared with 80 grams of Support I using the Catalyst Preparation Procedure. Sodium hydroxide was used as the precipitating agent. Following the reduction step, the liquid was drained from the catalyst beads and then the beads were rinsed quickly with a volume of water roughly equal to the catalyst volume. The catalyst was divided into four equal parts labelled Samples A, B, C, & D. Samples B, C and D were retained for use in the Examples which follow. Sample A was washed using the Batch Washing Procedure which involved covering the catalyst with 23 ml of deionized water and allowing it to stand for 36 minutes. The water was decanted and the catalyst covered with another 23 ml of fresh water. Washing was continued in this manner for a total of 5 washes done over a total of 3 hours. After the final wash, the beads were rinsed once with water then dried overnight at 60° C. The catalyst was analyzed for potassium (0.30%) and then impregnated with a solution of 0.955 g of potassium acetate in 11.7 ml of water. After drying at 60° C. overnight catalyst evaluation gave the results provided in Table C.

Run IV-2: Sample B from Run IV-1 above was washed batchwise a total of five times over three hours with 23 ml quantities of 5% aqueous potassium acetate solution using the same procedure as that specified in Run IV-1 above. After rinsing the beads with water the catalyst was dried overnight at 60° C. then analyzed for potassium (1.42%). The catalyst was then impregnated with a solution of 0.359 g of potassium acetate in 11.7 ml of water. After drying at 60° C. overnight catalyst evaluation gave the results provided in Table C.

Comparative Run IV-3: Sample C. from Run IV-1 above was washed five times with water in a manner identical to Run IV-1, above, except the duration of each wash was 96 minutes for a total of 8 hours washing time. Analysis for potassium showed 0.33% following washing. The sample was impregnated with a solution of 0.934 g of potassium acetate in 11.7 ml of water then dried overnight at 60° C. Test results are provided in Table C.

Run IV-4 Sample D from Run IV-1 above was washed five times with 5% potassium acetate solution using the procedure of Run IV-3 above. Analysis for potassium showed 1.69% following washing. The sample was impregnated with a solution of 0.216 g of potassium acetate in 11.7 ml of water then dried overnight at 60° C. Test results are provided in Table C.

TABLE C

| Effect of Potassium Acetate Batch Washing on Performance | | | |
|---|---|---|---|
| Run | % K | % Na | STY |
| IV-1* | 2.2 | 0.47 | 512 |
| IV-2 | 2.4 | 0.22 | 531 |
| IV-3* | 2.1 | 0.47 | 535 |
| IV-4 | 2.2 | 0.19 | 573 |

*Comparative Example

EXAMPLE V

Figure 2:
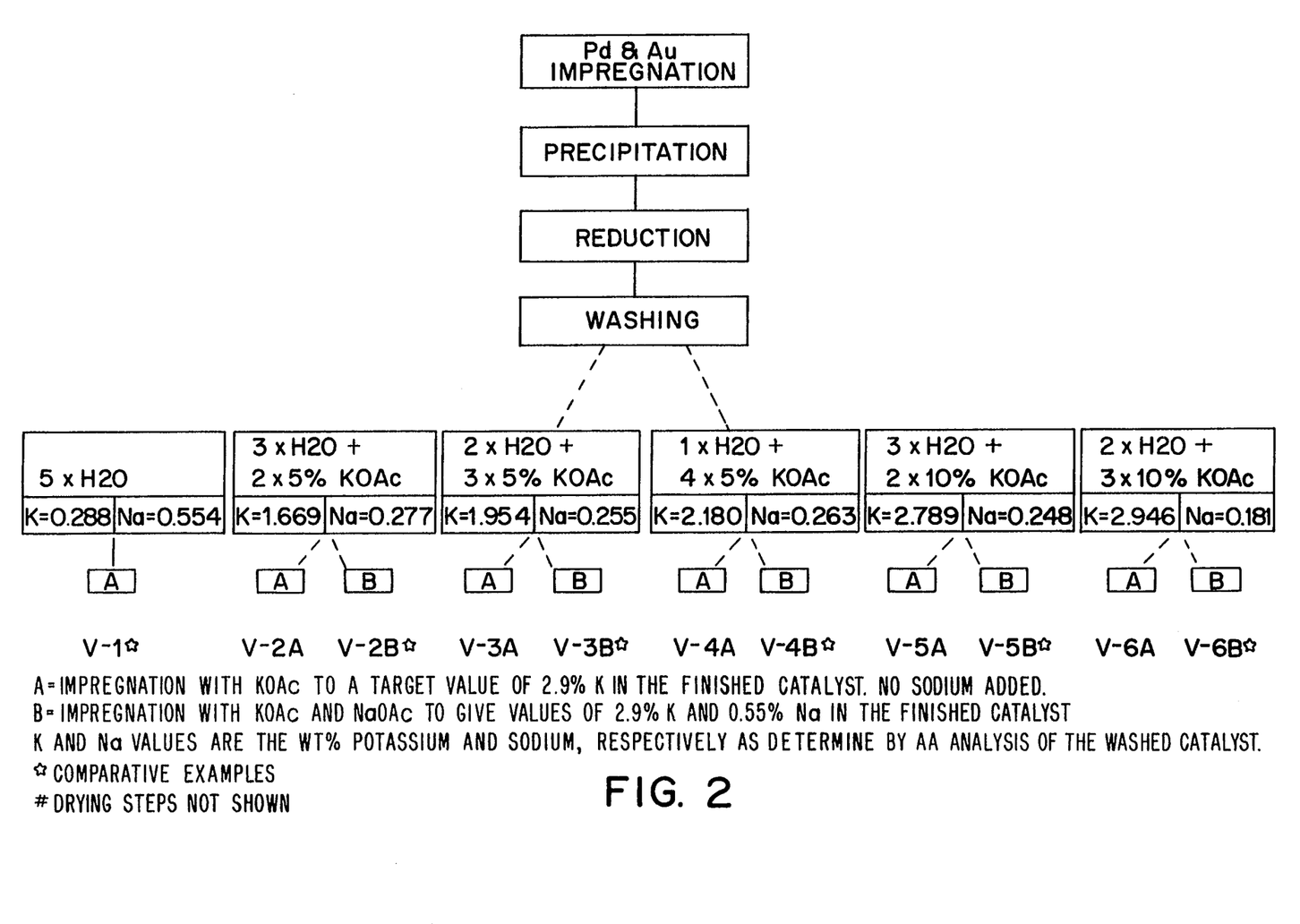
FIG. 2 shows various batch-washing experiments in accordance with this invention.

A further set of experiments was conducted to determine the most cost-effective quantity of potassium acetate required to give a significant activity improvement. In these experiments, a large batch of catalyst was divided just prior to the washing step (i.e., step (d) of the process of this invention) into six equal portions as shown in FIG. 2. All catalysts were batch washed a total of five times using the Batch Washing Procedure. The compositions of the washing solutions were varied as indicated in FIG. 2. For example, the first catalyst portion was batch washed five times with water; the second portion was washed three times with water followed by two times with 5% potassium acetate solution, etc. The catalysts were dried and analyzed by Atomic Absorption Spectroscopy for potassium and sodium. Each catalyst was again subdivided into "A" and "B" fractions. Each fraction was then treated with sufficient potassium acetate to bring the potassium level to about 2.9% in the finished catalyst. Those catalyst fractions labeled "B" also received sufficient sodium acetate to return their final sodium levels back to about the same level found in the water-washed catalyst (e.g., the level in the water-washed catalyst of Run V-1 below).

Thus two sets of catalysts were obtained: one set (the "A" series) shows the effect of potassium acetate washing on catalyst performance; and the second set (the "B" series) shows that sodium removal adequately accounted for that effect. These results are summarized in Table D.

Comparative Run V-1: A catalyst was prepared using the Catalyst Preparation Procedure with 100 grams of Support I and sodium metasilicate. After the reduction step, the solution was decanted and the catalyst was rinsed four times with water. The solutions of the precipitating agent and reducing agent were drained and the still-damp catalyst was divided into six equal portions, labeled Samples A, B, C, D, E, and F. Samples B through F were retained for use in the following Examples. Sample A was batch washed five times with about 20 ml quantities of water for a total of 8 hours. After drying overnight at 60° C., the catalyst was impregnated with a solution of 1.098 g of potassium acetate in 9.6 ml of water and dried at 60° C. The finished catalyst, which had the calculated potassium and sodium content shown in Table D, was evaluated for vinyl acetate activity. The results are shown in Table D.

Run V-2: Sample B from Run V-1 above was batch washed in a manner identical to that Run, except the first three washes consisted of water and the last two consisted of 5% potassium acetate solution. After drying overnight at 60° C., the catalyst was divided equally. The first portion was impregnated with 0.26 g of potassium acetate in 4.6 ml of water. After drying at 60° C. the catalyst, which had the calculated composition provided in Table D (Run V-2A), gave the results provided in the same table. The second half of the sample was impregnated with a solution of 0.26 g of potassium acetate and 0.090 g of sodium acetate in 4.6 ml of water. The calculated composition and results are shown in Table D (Run V-2B).

Run V-3: Sample C from Run V-1 above was batch washed in a manner identical to that Run, except the first two washes consisted of water and the last three consisted of 5% potassium acetate solution. After drying overnight at 60° C., the catalyst was divided equally. The first portion was impregnated with 0.20 g of potassium acetate in 4.6 ml of water. After drying the catalyst, which had the calculated composition shown in Table D (Run V-3A), gave the results provided in the same table. The second half of the sample was impregnated with a solution of 0.20 g of potassium acetate and 0.097 g of sodium acetate in 4.6 ml of water. The calculated composition and test results are given in Table D (Run V-3B).

Run V-4: Sample D from Run V-1 above was batch washed in a manner identical to Run V-1 above, except that the first wash consisted of water and the last four consisted of 5% potassium acetate solution. After drying overnight at 60° C., the catalyst was divided equally. The first portion was impregnated with 0.155 g of potassium acetate in 4.6 ml of water. After drying the catalyst, which had the calculated composition provided in Table D (Run V-4A), gave the results provided in the same table. The second half of the sample was impregnated with a solution of 0.155 g of potassium acetate and 0.094 g of sodium acetate in 4.6 ml of water. The calculated composition after drying and test results are shown in Table D (Run V-4B).

Run V-5: Sample E from Run V-1 above was batch washed in a manner identical to Run V-1 above, except that the first three washes consisted of water and the last two consisted of 10% potassium acetate solution. After drying overnight at 60° C., the catalyst was divided equally. The first portion was impregnated with 0.032 g of potassium acetate in 4.6 ml of water. After drying the catalyst, which had the calculated composition provided in Table D (Run V-5A), gave the results provided in the same table. The second half of the sample was impregnated with a solution of 0.032 g of potassium acetate and 0.098 g of sodium acetate in 4.6 ml of water. The calculated composition after drying and test results are shown in Table D (Run V-5B).

Run V-6: Sample F from V-1 above was batch washed in a manner identical to V-1 above, except that the first two washes consisted of water and the last three consisted of 10% potassium acetate solution. After drying overnight at 60° C., the catalyst was divided equally. The first portion was dried and divided without further impregnation with potassium acetate. The catalyst, which had the calculated composition provided in Table D (Run V-6A) gave the results provided in the same table. The second half of the sample was impregnated with a solution of 0.12 g of sodium acetate in 4.6 ml of water. The calculated composition after drying and test results are shown in Table D below (Run V-6B).

TABLE D

Batch-Washing Studies

| Run No. | % K(a) | % Na(a) | STY | % Selectivity | Washing Liquids and Sequence |
|---|---|---|---|---|---|
| Sodium Reduced - "Series A" |||||| 
| V-1* | 2.83 | 0.518 | 527 | 93.7 | 5x H2O |
| V-2A | 2.87 | 0.268 | 603 | 93.3 | 3x H2O plus 2x 5% KOAc |
| V-3A | 2.88 | 0.249 | 615 | 93.2 | 2x H2O plus 3x 5% KOAc |
| V-4A | 2.90 | 0.258 | 630 | 93.2 | 1x H2O plus 4x 5% KOAc |
| V-5A | 2.94 | 0.247 | 604 | 93.3 | 3x H2O plus 2x 10% KOAc |
| V-6A | 2.95 | 0.181 | 571 | 93.5 | 2x H2O plus 3x 10% KOAc |
| Sodium Reduced Then Added - "Series B" |||||| 
| V-1* | 2.83 | 0.518 | 527 | 93.7 | 5x H2O |
| V-2B* | 2.84 | 0.554 | 516 | 93.6 | 3x H2O plus 2x 5% KOAc |
| V-3B* | 2.85 | 0.558 | 519 | 93.9 | 2x H2O plus 3x 5% KOAc |
| V-4B* | 2.86 | 0.561 | 534 | 93.5 | 1x H2O plus 4x 5% KOAc |
| V-5B* | 2.90 | 0.567 | 502 | 93.8 | 3x H2O plus 2x 10% KOAc |

TABLE D-continued

Batch-Washing Studies

| Run No. | % K(a) | % Na(a) | STY | % Selectivity | Washing Liquids and Sequence |
|---|---|---|---|---|---|
| V-6B* | 2.90 | 0.574 | 488 | 94.1 | 2x H2O plus 3x 10% KOAc |

(a)Estimated value. Calculated from the AA Analysis prior to KOAc/NaOAc impregnation and the quantities of acetates added.
*Comparative Examples Significant activity improvements are seen in Table D in the "Series A" catalysts (compare Run V-1 with Runs V-2A through V-6A) and these improvements are in general agreement with the lower sodium contents of these catalysts. The "Series B" catalysts show that the readdition of sodium to "Series A" catalysts suppresses catalyst activities back to the range of the original, water-washed catalyst (compare Run V-1 with Runs V-2B through V-6B). These results again support the theory that removal of sodium is responsible for the observed activity gains.

EXAMPLE VI

Ion chromatography was used to analyze the effluents from the Column Washing Procedure and Batch Washing Procedure from several catalyst preparations. These involved the use of both water and potassium acetate solutions as the wash liquids and were done in an effort to detect any impurity which might go undetected by ICP analyses. Sulfate appeared to be the major impurity, yet was estimated to be less than 100 ppm in the original catalyst. Smaller levels of phosphate and chloride were also detected. To determine whether sulfate might have a detrimental effect on activity, potassium sulfate was added in amounts of 500 and 1000 ppm to two catalysts. The effect on activity was insignificant as is shown in Table E.

TABLE E

Effect of Added Sulfate

| Sulfate(a) | STY | % Selectivity |
|---|---|---|
| 0 | 550 | 93.8 |
| 500 | 552 | 93.9 |
| 1000 | 577 | 93.8 |

(a)ppm of potassium sulfate added with the potassium acetate promoter.

Figure 3:
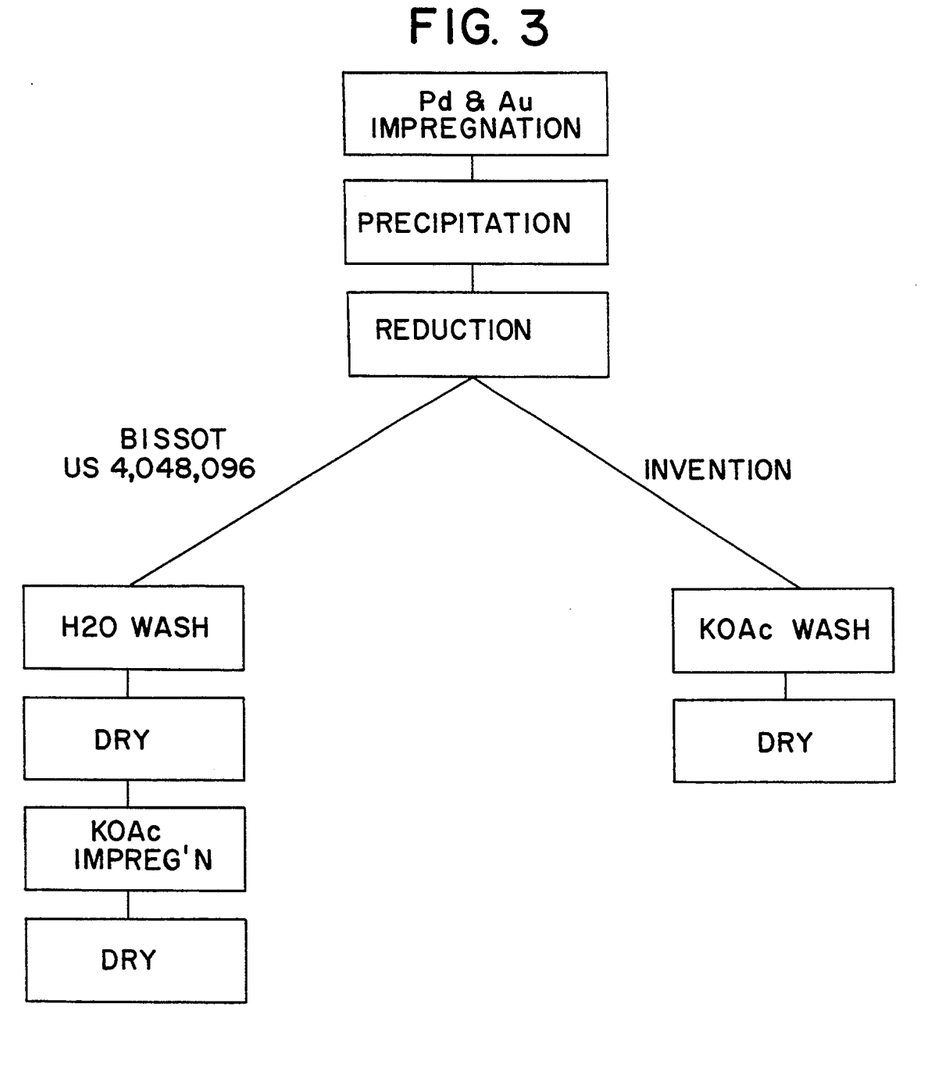
FIG. 3 shows the vinyl acetate catalyst preparation procedure of U.S. Pat. No. 4,048,096 and the catalyst preparation procedure of the preferred embodiment of this invention.

Examples VII to XII below illustrate the preferred embodiment of this invention that is shown in FIG. 3.

Example VII

Using the Catalyst Preparation Procedure, a catalyst was prepared on 50 g of Support I using sodium hydroxide as the precipitating agent. After the reduction step, the liquid was drained from the catalyst and the beads were rinsed four times with water to remove metal sludge. The damp catalyst was divided into three equal portions labeled Samples A, B, and C. Samples B and C. were retained for use in the following Examples. Sample A was washed five times with 23-ml quantities of 5% potassium acetate solution for a total of 8 hours using the Batch Washing Procedure of Run IV-4 above. Each wash was of 96 minutes duration. The catalyst was dried at 60° C. without rinsing with water, and evaluated for vinyl acetate activity without further addition of potassium acetate. The analysis and test results are shown in Table F.

Example VIII

Sample B prepared in Example VII above was washed as described in that Example, except that the first four washes with 5% potassium acetate had a duration of 1 hour each and the final wash had a duration of 4 hours. The catalyst was dried at 60° C. without rinsing with water. The analysis and test results are shown in Table F.

Example IX

Sample C prepared in Example VII above was washed as described in that Example, except that 7% potassium acetate solution was used. The catalyst was dried at 60° C. without rinsing with water. The analysis and test results are shown in Table F.

Comparative Example X

A 20-liter quantity of catalyst was prepared in a pilot plant using the Catalyst Preparation Procedure and water washed using the Batch Washing Procedure. The analysis and test results are shown in Table F.

Example XI

A 20-liter catalyst sample was prepared using the process described in Example VII above. The analysis and test results are shown in Table F.

Example XII

A 520-liter catalyst sample was prepared in a commercial production unit using the process described in Example VII above. The analysis and test results are shown in Table F.

TABLE F

Performance of Catalysts Prepared Using the Five-Step Preparation Procedure

| RUN | % Pd | % Au | % K | % Na | STY |
|---|---|---|---|---|---|
| IV-3* | 0.54 | 0.19 | 2.2 | 0.47 | 535 |
| VII | — | 0.20 | 2.5 | 0.10 | 643 |
| VIII | 0.57 | 0.22 | 2.5 | 0.11 | 645 |
| IX | 0.56 | 0.22 | 2.9 | 0.10 | 592 |
| X* | 0.53 | 0.20 | 2.3 | 0.73 | 587 |
| XI | 0.56 | 0.26 | 2.9 | 0.12 | 695 |
| XII | 0.56 | 0.25 | 3.0 | 0.18 | 666 |

*Comparative Examples (seven-step preparations)

The data in Table F shows the improvements achieved with this invention.

Example XIII

A sample of catalyst from Example XII above was impregnated with potassium acetate solution at a concentration calculated to increase the potassium loading by about 0.8%. The resulting catalyst contained 0.56% Pd, 0.25% Au, 3.7% K and 0.17 Na % and had an STY of 550.

Example XIV

The effect of sodium on the performance of vinyl acetate catalysts was studied using statistically designed experiments and models were obtained which are useful in predicting the performance of the vinyl acetate catalysts produced by the process of this invention as well as vinyl acetate catalysts produced by the processes of U.S. Pat. No. 5,189,004 and U.S. Pat. No. 5,179,056. The models predict catalyst activity and selectivity as a function of sodium content, palladium loading, gold to palladium weight ratio, potassium content and catalyst weight. These models and the data from which they were generated are shown in Tables G and H respectively.

Figure 4:
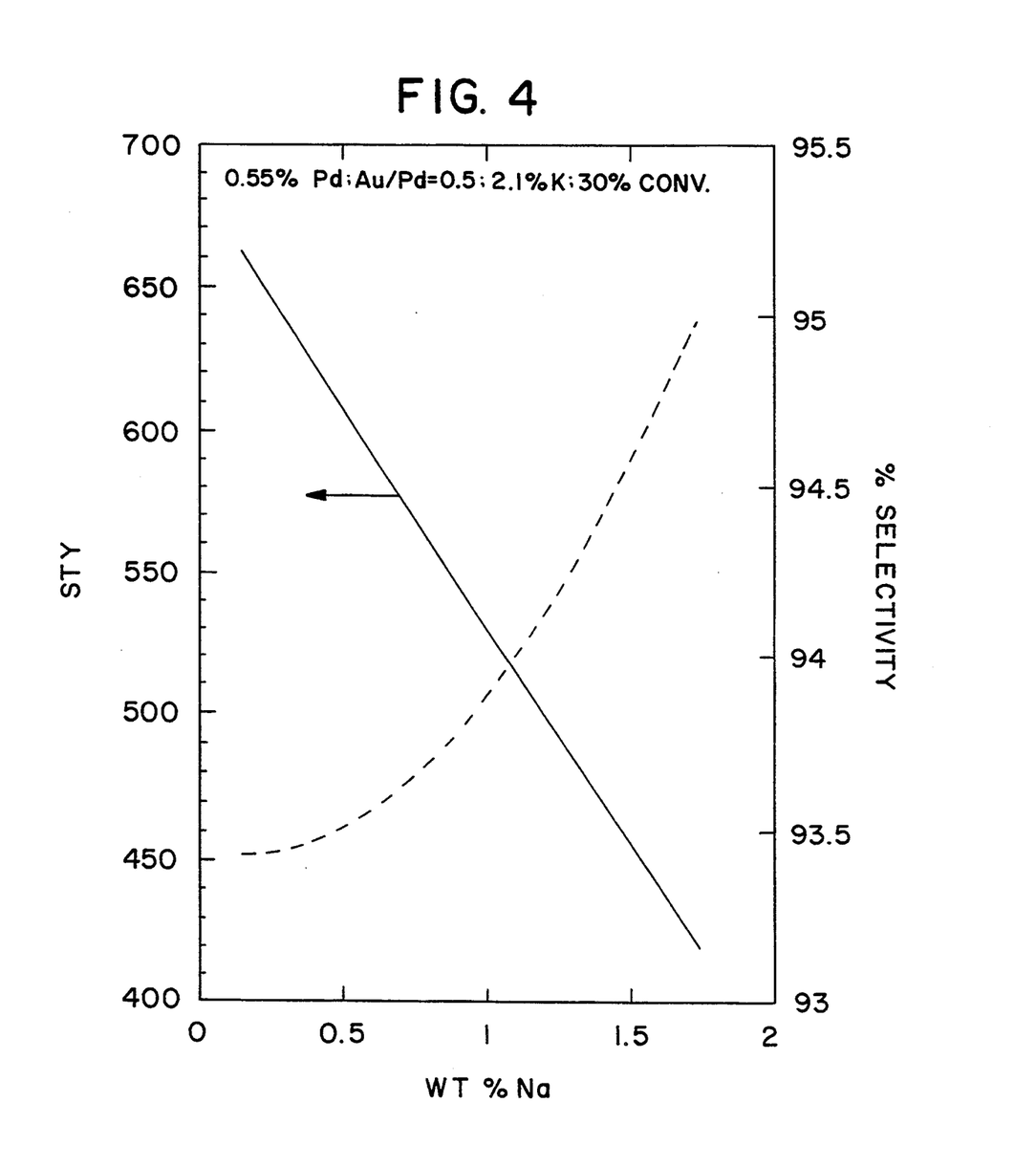
FIG. 4 shows the predicted effect of sodium on the performance of vinyl acetate catalysts produced in accordance with this invention.

Because the degree of conversion has a major effect on both catalyst productivity and selectivity, meaningful comparisons of catalyst variables can only be done at constant conversion. In order to predict the effects of catalyst composition at constant conversion, the Oxygen Conversion Model in Table G was rearranged to express catalyst weight as a function of the palladium content, gold/palladium ratio, potassium content, sodium content and conversion. This catalyst weight term was then used to replace the catalyst weight terms in the STY and Selectivity models. The predicted effects of increasing sodium content on vinyl acetate catalyst activity and selectivity are plotted in FIG. 4.

The abbreviations used in Tables G and H have the following meanings:

| | |
|---|---|
| Pd = | Weight percent palladium in the catalyst |
| Au/Pd = | Weight ratio of gold to palladium in the catalyst |
| Cat. Wt = | Catalyst weight in grams |
| K = | Weight percent potassium in the catalyst |
| Na = | Weight percent sodium in the catalyst |
| STY = | Space time yield in grams of vinyl acetate per liter of catalyst per hour |
| $R^2$ = | Correlation coefficients which areindicative of the quality of fit of the data to the models |
| RSD = | Relative standard derivation |
| EtOAc By-Product Rate = | Production of ethyl acetate in moles/kilogram of catalyst/hour |
| % Heavies By Products in VA = | Heavy by-products expressed as a weight percent of the vinyl acetate produced. Heavies by-products are defined as all products which elute after acetic acid in the gas chromatographic analytical procedure. |

Table I below shows the effect of varying sodium on catalyst activity as predicted by the models in Table G.

TABLE G

MODELS RELATING PERFORMANCE TO CATALYST COMPOSITION(a)

Part A $O_2$ Conversion to Vinyl Acetate = $100/(1 + e^{Z1})$

Where Z1 = 0.507 − 1.907(% Pd − 0.743) − 0.863(Au/Pd − 0.584) + 0.109(% K − 2.43) + 0.459(% Na − 0.502) −
(19.6) (8.1) (4.5) (7.0)
.913(Cat. Wt. − 1.91) + 1.438(% Pd − 0.743)(Au/Pd − 0.584) + 0.551(Au/Pd − 0.584)(Cat. Wt. − 1.91) +
(29.8) (3.9) (5.1)
1.438(% Pd − 0.743)$^2$ + 2.779(Au/Pd − 0.584)$^2$ + 1.384(% K − 2.43)$^2$ + 0.284(Cat Wt. − 1.91)$^2$
(3.1) (4.2) (4.4) (6.5)

$R^2$ = 0.988
RSD = 0.103

Part B

TABLE G-continued
MODELS RELATING PERFORMANCE TO CATALYST COMPOSITION(a)

Activity (STY) = $e^{Z2}$

Where $Z2 = 6.707 + 0.942(\%\ Pd - 0.743) + 0.334(Au/Pd - 0.584) - 0.194(\%\ Na - 0.502) - 0.123(Cat.\ Wt. - 1.91) -$
(13.6) (5.6) (4.0) (8.1)
$1.438(\%\ Pd - 0.743)^2 - 0.128(\%\ K - 2.43)^2$
(4.3) (5.6)

$R^2 = 0.922$
$RSD = 0.079$

Part C
Selectivity to Vinyl Acetate = $100 - e^{Z3}$

Where $Z3 = 1.9 + 0.457(\%\ Pd - 0.743) - 0.118(\%\ K - 2.43) - 0.095(\%\ Na - 0.502) + 0.121(Cat.\ Wt. - 1.91) +$
(17.4) (12.7) (3.5) (14.8)
$0.186(\%\ Pd - 0.743)(Cat.\ Wt. - 1.91) - 0.254(Au/Pd - 0.584)(\%\ K - 2.43) - 0.0525(\%\ K - 2.43)(Cat.$
(5.9) (6.3) (4.6)
$Wt. - 1.91) - 0.164(\%\ Na - 0.502)(Cat.\ Wt. - 1.91) + 0.038(\%\ K - 2.43)^2$
(4.1) (3.2)

$R^2 = 0.956$
$RSD = 0.034$

Part D
EtOAc By-Product Rate = $e^{Z4}$

Where $Z4 = -3.640 + 0.9175(\%\ Pd - 0.743) - 1.135(Au/Pd - 0.584) - 0.2189(Cat.\ Wt. - 1.91) - 0.3743(\%\ Na - 0.502) -$
(7.5) (10.7) (8.1) (6.4)
$0.267(\%\ K - 2.43)^2 - 2.428(\%\ Pd - 0.743)^2$
(7.2) (4.1)

$R^2 = 0.872$
$RSD = 0.142$

Part E
% Heavies By-Product in VA = $e^{Z5}$(b)

Where $Z5 = 0.280 + 0.441(Au/Pd - 0.584) - 0.254(\%\ K - 2.43) - 0.0694(Cat.\ Wt. - 1.91)$
(5.2) (10.5) (3.1)

$R^2 = 0.797$
$RSD = 0.119$ (a)Values in parentheses beneath the regression equations are the observed T-ratios.
(b)Based on the amount of vinyl acetate produced.

TABLE H

| No. | % Pd | Au/Pd | % K | % Na | Cat Wt. | % O$_2$ Conv | STY | % Selectivity |
|---|---|---|---|---|---|---|---|---|
| DESIGN DATA(a) | | | | | | | | |
| 1 | 0.80 | 0.70 | 2.23 | 0.51 | 1.64 | 34.4 | 897.6 | 93.2 |
| 2 | 0.80 | 0.70 | 2.23 | 0.51 | 1.65 | 37.1 | 941.5 | 92.9 |
| 3 | 0.80 | 0.70 | 2.23 | 0.51 | 1.65 | 34.8 | 923.3 | 93.2 |
| 4 | 1.05 | 0.91 | 3.67 | 0.26 | 0.73 | 16.1 | 1181.7 | 94.4 |
| 5 | 0.57 | 0.46 | 2.33 | 0.14 | 0.73 | 7.1 | 759.2 | 94.6 |
| 6 | 0.54 | 0.89 | 2.27 | 0.16 | 2.50 | 44.9 | 727.4 | 92.5 |
| 7 | 1.13 | 0.96 | 2.35 | 0.18 | 0.75 | 21.0 | 1262.4 | 94.1 |
| 8 | 0.52 | 0.44 | 3.51 | 0.17 | 0.76 | 5.8 | 553.2 | 94.5 |
| 9 | 1.14 | 0.46 | 2.35 | 0.19 | 2.50 | 66.1 | 912.3 | 89.7 |
| 10 | 0.53 | 0.91 | 3.64 | 0.14 | 2.51 | 32.7 | 595.0 | 94.4 |
| 11 | 1.05 | 0.47 | 3.68 | 0.18 | 2.50 | 55.7 | 847.4 | 92.1 |
| 12 | 1.08 | 0.87 | 2.80 | 0.73 | 0.76 | 17.5 | 1158.0 | 93.8 |
| 13 | 0.52 | 0.46 | 1.50 | 0.37 | 0.72 | 6.6 | 569.0 | 94.0 |
| 14 | 0.52 | 0.85 | 1.40 | 0.50 | 2.50 | 38.4 | 587.4 | 91.5 |
| 15 | 1.08 | 0.94 | 1.40 | 0.54 | 0.74 | 19.3 | 1111.7 | 92.1 |
| 16 | 0.55 | 0.42 | 2.70 | 0.44 | 0.76 | 5.9 | 617.2 | 94.3 |
| 17 | 1.10 | 0.45 | 1.40 | 0.59 | 2.54 | 57.7 | 769.9 | 89.7 |
| 18 | 0.55 | 0.91 | 2.90 | 0.40 | 2.54 | 34.7 | 629.5 | 94.1 |
| 19 | 1.09 | 0.47 | 2.80 | 0.50 | 2.52 | 56.6 | 865.0 | 91.5 |
| 20 | 0.82 | 0.70 | 2.12 | 0.49 | 1.63 | 35.2 | 901.9 | 93.0 |
| 21 | 0.82 | 0.70 | 2.12 | 0.49 | 1.62 | 35.7 | 925.7 | 92.9 |
| 22 | 0.78 | 0.65 | 2.12 | 0.53 | 2.52 | 50.6 | 793.2 | 92.2 |
| 23 | 0.78 | 0.65 | 2.12 | 0.53 | 1.63 | 33.3 | 884.2 | 93.4 |
| 24 | 1.07 | 0.83 | 2.93 | 0.69 | 2.53 | 51.8 | 822.1 | 92.5 |
| 25 | 0.53 | 0.36 | 2.96 | 0.44 | 2.52 | 28.5 | 506.7 | 93.4 |
| 26 | 1.07 | 0.82 | 1.47 | 0.56 | 2.50 | 54.3 | 709.7 | 88.7 |
| 27 | 1.07 | 0.82 | 1.47 | 0.56 | 2.51 | 52.4 | 701.7 | 89.3 |
| 28 | 0.56 | 0.82 | 3.02 | 0.42 | 0.75 | 7.7 | 733.8 | 95.0 |
| 29 | 1.02 | 0.46 | 2.88 | 0.48 | 0.75 | 14.1 | 966.6 | 93.8 |
| 30 | 0.54 | 0.44 | 1.51 | 0.36 | 2.50 | 29.6 | 483.5 | 92.7 |
| 31 | 0.54 | 0.80 | 1.48 | 0.50 | 0.75 | 10.8 | 763.7 | 94.0 |
| 32 | 1.08 | 0.43 | 1.47 | 0.63 | 0.75 | 13.1 | 889.6 | 93.2 |
| 33 | 0.80 | 0.66 | 2.12 | 0.92 | 1.64 | 33.0 | 871.5 | 93.2 |
| 34 | 0.80 | 0.66 | 2.12 | 0.92 | 1.62 | 32.3 | 866.4 | 93.5 |
| 35 | 1.13 | 0.62 | 2.10 | 0.59 | 1.62 | 43.1 | 1066.2 | 92.4 |
| 36 | 0.41 | 0.61 | 2.20 | 0.37 | 1.64 | 21.3 | 621.8 | 94.2 |
| 37 | 0.76 | 0.87 | 2.10 | 0.55 | 1.62 | 33.3 | 881.8 | 93.7 |
| 38 | 0.76 | 0.34 | 2.10 | 0.45 | 1.65 | 27.5 | 734.0 | 93.4 |
| 39 | 0.77 | 0.61 | 2.10 | 0.52 | 0.43 | 9.9 | 1246.7 | 93.7 |
| 40 | 0.77 | 0.61 | 2.10 | 0.52 | 2.86 | 56.9 | 745.8 | 91.7 |
| Supplemental Data(b) | | | | | | | | |
| 41 | 0.56 | 0.39 | 2.19 | 0.44 | 2.54 | 36.0 | 607.8 | 93.5 |
| 42 | 0.57 | 0.39 | 2.19 | 0.15 | 2.54 | 38.4 | 612.0 | 92.7 |
| 43 | 0.54 | 0.39 | 3.38 | 0.68 | 2.54 | 25.8 | 482.8 | 94.1 |
| 44 | 0.55 | 0.39 | 3.38 | 0.28 | 2.54 | 30.9 | 545.9 | 93.5 |
| 45 | 0.56 | 0.39 | 2.79 | 0.28 | 2.54 | 36.4 | 605.5 | 93.4 |
| 46 | 0.56 | 0.39 | 2.79 | 0.16 | 2.54 | 37.2 | 610.9 | 92.9 |
| 47 | 0.54 | 0.39 | 2.79 | 0.96 | 2.54 | 27.4 | 493.2 | 93.8 |
| 48 | 0.54 | 0.39 | 3.62 | 0.36 | 2.54 | 27.2 | 492.4 | 93.7 |
| 49 | 0.57 | 0.39 | 1.95 | 0.20 | 2.54 | 35.3 | 571.0 | 92.9 |
| 50 | 0.54 | 0.39 | 3.70 | 0.39 | 2.54 | 27.1 | 483.8 | 93.9 |
| 51 | 0.55 | 0.39 | 2.12 | 1.25 | 2.54 | 27.4 | 494.1 | 94.1 |
| 52 | 0.50 | 0.39 | 3.95 | 2.39 | 2.54 | 13.4 | 283.9 | 94.3 |
| 53 | 0.56 | 0.39 | 2.25 | 0.50 | 2.54 | 33.6 | 609.3 | 93.5 |
| 54 | 0.57 | 0.39 | 2.25 | 0.12 | 2.54 | 34.9 | 641.5 | 93.1 |
| 55 | 0.55 | 0.39 | 2.25 | 1.01 | 2.54 | 28.7 | 540.0 | 94.1 |

(a)Unless otherwise indicated, the palladium and gold values were determined by ICP and the sodium and potassium values were determined by Atomic Absorption Analysis.
(b)The catalysts were prepared by addition of sodium and potassium acetates to Catalyst II that had been rewashed as described in U.S. Pat. No. 5,189,004.

TABLE I
Predicted Effect of Sodium on Catalyst* Activity

| % Na | STY | % Improvement** |
|---|---|---|
| 0.1 | 665 | 0.0 |
| 0.2 | 649 | 2.5 |
| 0.3 | 633 | 5.1 |
| 0.4 | 618 | 7.6 |
| 0.5 | 603 | 10.3 |
| 0.6 | 581 | 14.5 |
| 0.7 | 574 | 15.9 |
| 0.8 | 560 | 18.8 |
| 0.9 | 546 | 21.8 |

*For a catalyst composition set at: 0.58% Pd, Au/Pd = 0.45 and 2.2% K and an oxygen conversion set at 35%.
**Predicted percent change in STY resulting from decrease in sodium content from amount shown in first column to 0.1%.

The purpose of Examples XV to XXX below was to demonstrate the utility of various cation exchange solutions in this invention.

Comparative Example XV

A catalyst was prepared using the catalyst preparation procedure with 90 grams of support and sodium hydroxide as the precipitating agent. Following the reduction step, the catalyst was drained and the beads were rinsed four times with water. The damp catalyst was divided into six equal portions labelled Samples A, B, C, D, E and F. Samples B through F were retained for use in the examples which follow. Sample A was washed with five 20-ml portions of water using the Batch Washing Procedure as set out in Run IV-3 above. Evaluation of the finished catalyst gave the results shown in Table J.

Example XVI

Sample B from Example XV above was washed with 20-ml portions of 2% ammonium carbonate in water using the procedure described in that Example. Evaluation of the finished catalyst gave the results shown in Table J.

Example XVII

Sample C from Example XV above was washed with 20-ml portions of 2% lithium acetate in water using the procedure described in that Example. Evaluation of the catalyst gave the results shown in Table J. The lithium content of the finished catalyst was found to be 0.18% by AA analysis.

Comparative Example XVIII

Sample D from Example XV above was washed with 20-ml portions of 2% sodium acetate in water using the procedure described in that Example. Catalyst evaluation gave the results in Table J.

Example XIX

Sample E from Example XV above was washed with 20-ml portions of 2% potassium nitrate in water using the procedure described in that Example. Catalyst evaluation gave the results in Table J.

Example XX

Sample F from Example XV above was washed with 20-ml portions of 2% potassium carbonate in water using the procedure described in that Example. Results of catalyst evaluation are shown in Table J.

TABLE J

Effect of Various Cation Exchange Solutions on Catalyst Activity

| Example | Salt | % Pd | % Au | % K | % Na | STY |
|---|---|---|---|---|---|---|
| XV* | None | 0.58 | 0.22 | 2.23 | 0.37 | 474** |
| XVI | (NH4)2CO3 | 0.58 | 0.22 | 2.20 | 0.13 | 527 |
| XVII | LiOAc | 0.58 | 0.23 | 2.22 | 0.19 | 486 |
| XVIII* | NaOAc | 0.57 | 0.22 | 2.26 | 0.79 | 447 |
| XIX | KNO3 | 0.59 | 0.23 | 2.26 | 0.13 | 492 |
| XX | K2CO3 | 0.59 | 0.23 | 3.06 | 0.14 | 523 |

*Comparative Examples
**Average of three runs having STY's of 453, 498 & 470.

Comparative Example XXI

Catalysts were prepared according to the procedure of Example XV above. Following reduction, the damp catalyst was divided into six equal portions labelled Samples A, B, C, D, E, and F. Samples B through F were retained for use in the Examples which follow. Sample A was washed with five 20-ml portions of water as described in Example XV above. Catalyst evaluation gave the results shown in Table K.

Example XXII

Sample B from Example XXI above was washed with 20-ml portions of 2% ammonium acetate in water as described in Example XV above. Catalyst evaluation gave the results shown in Table K.

Example XXIII

Sample C from Example XXI above was washed with 20-ml portions of 2% potassium acetate in water as described in Example XV above. Catalyst evaluation gave the results shown in Table K.

Example XXIV

Sample D from Example XXI above was washed with 20-ml portions of 2% potassium sulfate in water as described in Example XV above. Catalyst evaluation gave the results in shown Table K. The potassium sulfate solution is a less suitable cation exchange solution because it apparently converts to the effective species (potassium acetate) relatively slowly.

Example XXV

Sample F from Example XXI above was washed with 20-ml portions of 2% magnesium acetate in water using the procedure described in Example XV. Catalyst evaluation gave the results shown in Table K.

TABLE K

Effect of Various Cation Exchange Solutions on Catalyst Activity

| Example | Salt | % Pd | % Au | % K | % Na | STY |
|---|---|---|---|---|---|---|
| XXI* | None | 0.560 | 0.196 | 2.27 | 0.52 | 523 |
| XXII | NH4OAc | 0.576 | 0.187 | 2.49 | 0.11 | 594 |
| XXIII | KOAc | 0.613 | 0.209 | 2.13 | 0.13 | 561 |
| XXIV | K2SO4 | 0.618 | 0.216 | 2.13 | 0.12 | 493** |
| XXV | Mg(OAc)2 | 0.573 | 0.225 | 2.39 | 0.17 | 575 |

*Comparative Examples
**There was insufficient reaction time to show the effectiveness of this cation exchange solution.

EXAMPLE XXVI

The activities of three commercial catalysts (Catalysts X, Y and Z) are shown in Table L. In Table L, the measured activities of Catalysts X and Y are compared to the predicted activities of catalysts of this invention having the same composition ("Model Catalysts"). The predicted activities were determined from the models of Table G and assuming a 0.15% level of sodium. The Model Catalyst had markedly higher predicted activities. A similar comparison could not be made for Catalyst Z because its composition is outside the range of the models of Table G.

Catalyst X was prepared using the Catalyst Preparation Procedure. The preparation of Catalyst X differed from the preparation of Catalyst Y in that, in the preparation of Catalyst Y: (1) the catalyst was dried before precipitation and (2) the precipitating agent used was sodium hydroxide rather than sodium metasilicate. The reduction, washing, drying and potassium acetate impregnation steps were the same for both catalyst preparations.

With reference to Catalyst Y, the suffixes A, B and C in Table L denote different preparations ("lots") of nominally the same catalyst and, with respect to Catalysts Y and Z the suffixes 1 and 2 denote duplicate analyses of different samples from the same lot of the catalysts.

Catalyst Z has a high palladium content and uses a cadmium co-catalyst rather than gold. Cadmium is significantly more toxic than gold. In addition, catalyst Z is prepared by a process substantially different from the process of this invention. That is, Catalyst Z is prepared by impregnating a support with a solution of palladium, cadmium and potassium acetates and drying. There are no precipitation, reduction or washing steps in the process used to produce Catalyst Z.

TABLE L

|  | % Pd | % Au | % Cd | % K | % Na | STY |
|---|---|---|---|---|---|---|
| Catalyst X* | 0.53 | 0.22 | 0 | 2.36 | 0.54 | 272 |
| Model Catalyst | 0.53 | 0.22 | 0 | 2.36 | 0.15 | 589 |
| Catalyst YA-1* | 0.49 | 0.19 | 0 | 2.29 | 0.60 | 360 |
| Model Catalyst | 0.49 | 0.19 | 0 | 2.29 | 0.15 | 546 |
| Catalyst YA-2* | 0.49 | 0.19 | 0 | 2.31 | 0.60 | 360 |
| Model Catalyst | 0.49 | 0.19 | 0 | 2.31 | 0.15 | 545 |
| Catalyst YB* | 0.63 | 0.24 | 0 | 2.27 | 0.70 | 386 |
| Model Catalyst | 0.63 | 0.24 | 0 | 2.27 | 0.15 | 669 |
| Catalyst YC-1* | 0.61 | 0.24 | 0 | 2.24 | 0.69 | 395 |
| Model Catalyst | 0.61 | 0.24 | 0 | 2.24 | 0.15 | 653 |
| Catalyst YC-2* | 0.61 | 0.26 | 0 | 2.18 | 0.70 | 395 |
| Model Catalyst | 0.61 | 0.26 | 0 | 2.18 | 0.15 | 658 |
| Catalyst Z-1* | 2.16 | 0 | 1.88 | 1.89 | 0.08 | 685 |
| Model Catalyst | | | Outside range of models | | | |
| Catalyst Z-2* | 2.16 | 0 | 1.89 | 1.92 | 0.09 | 685 |
| Model Catalyst | | | Outside range of models | | | |

*Comparative catalysts

COMPARATIVE EXAMPLE XXVII

The procedure of Example 1 of U.S. Pat. No. 4,048,096 (Bissot) was repeated twice as follows: Two preparations (Runs 1 and 2) were made, each employing 15g of Support I, 0.315 g of $Na_2PdCl_4$, 0.085 g of $HAuCl_4$, 0.585 g of $Na_2SiO_3 \cdot 9H_2O$, 0.59 g of 85% hydrazine hydrate, and 0.823 g of potassium acetate. Since the exact washing procedure is not disclosed in Example 1 of Bissot, the catalyst of Run 1 was washed using the Column Washing Procedure for 16 hours using 23 ml of $H_2O$ per gram of catalyst whereas the catalyst of Run 2 was similarly washed but with 31 ml of $H_2O$ per gram of catalyst. The catalysts so produced were analyzed by ICP for palladium and gold and by AA Analysis for potassium and sodium. The experimental error of the sodium determination is estimated to be about ±0.01 relative percent. The catalyst of Run 1 was analyzed in duplicate. The results are shown in Table M.

TABLE M

|  | % Pd | % Au | % K | % Na | STY | Selectivity |
|---|---|---|---|---|---|---|
| Run 1* | 0.544 | 0.201 | 2.34 | 0.32 | 550 | 93.9 |
| Run 1* | 0.556 | 0.204 | 2.35 | 0.32 |  |  |
| Run 2* | 0.552 | 0.195 | 2.34 | 0.38 | 535 | 93.7 |
| Bissot | 0.578* | 0.242* | 2.08* | — | 560** | 93** |

*Calculated based on data in Example 1 of Bissot
**Disclosed in Example 1 of Bissot

What is claimed is:

1. A process for producing an alkenyl alkanoate which comprises reacting an alkene, an alkanoic acid and an oxygen-containing gas in the presence of a catalytic amount of a catalyst that is useful in catalyzing the reaction of an alkene, an alkanoic acid and an oxygen-containing gas to produce an alkenyl alkanoate and that comprises support particles which are capable of exchanging cations and which are impregnated with precipitated and reduced palladium and gold and a potassium promoter, any sodium in the catalyst being present in an amount no more than 0.3 weight precent based on the weight of the catalyst.

* * * * *